(12) United States Patent
Nakamura et al.

(10) Patent No.: US 11,052,191 B2
(45) Date of Patent: Jul. 6, 2021

(54) SYRINGE PUMP

(71) Applicant: MINEBEA MITSUMI Inc., Nagano (JP)

(72) Inventors: Manabu Nakamura, Toshimaku (JP); Koichi Yaeguchi, Sumidaku (JP)

(73) Assignee: MINEBEA MITSUMI INC., Nagano (JP)

( * ) Notice: Subject to any disclaimer, the term of this patent is extended or adjusted under 35 U.S.C. 154(b) by 125 days.

(21) Appl. No.: 16/402,416

(22) Filed: May 3, 2019

(65) Prior Publication Data

US 2019/0255249 A1 Aug. 22, 2019

Related U.S. Application Data

(63) Continuation of application No. PCT/JP2017/037689, filed on Oct. 18, 2017.

(30) Foreign Application Priority Data

Nov. 11, 2016 (JP) .............................. JP2016-220377

(51) Int. Cl.
*A61M 5/145* (2006.01)
*A61M 5/315* (2006.01)
*A61M 5/142* (2006.01)

(52) U.S. Cl.
CPC .......... *A61M 5/1458* (2013.01); *A61M 5/145* (2013.01); *A61M 5/31513* (2013.01); *A61M 5/14216* (2013.01)

(58) Field of Classification Search
CPC .. F16H 25/20; F16H 25/2003; F16H 25/2025; A61M 5/1458; A61M 5/1456; A61M 5/145; A61M 5/1452; A61M 5/5086; A61M 5/2053; A61M 5/31515; A61M 5/14216; A61M 5/14526; A61M 5/14506; A61M 5/14573; A61M 5/14236
See application file for complete search history.

(56) References Cited

U.S. PATENT DOCUMENTS 5,101,679 A * 4/1992 Smith ................. A61M 5/1456
128/DIG. 1

FOREIGN PATENT DOCUMENTS

| JP | 59-188436 U | 12/1984 |
| JP | 03-247347 A | 11/1991 |
| JP | 06-055644 U | 8/1994 |

OTHER PUBLICATIONS

International Search Report for corresponding International Application No. PCT/JP2017/037689 dated Jan. 16, 2018.

(Continued)

*Primary Examiner* — Bhisma Mehta
*Assistant Examiner* — John J Crawford
(74) *Attorney, Agent, or Firm* — Pearne & Gordon LLP

(57) ABSTRACT

A syringe pump according to an embodiment includes a lead screw and a slider. The slider has an engagement part that engages with the lead screw and a slider cover with an internal space that houses the engagement part and is formed therein and an external surface that contacts a plunger of a syringe, and slides to move in a predetermined direction of travel with rotation of the lead screw to push the plunger. Then, the slider cover has a contact part that is provided in the internal space and contacts, when the slider pushes the plunger, a location that is close to the engagement part where the location is provided on a side of the direction of travel.

5 Claims, 6 Drawing Sheets

(56) References Cited

OTHER PUBLICATIONS

Written Opinion for corresponding International Application No. PCT/JP2017/037689 dated Jan. 16, 2018.
Notice of Reasons for Refusal dated Dec. 2, 2020 for corresponding Japanese Application No. 2016-220377 and English translation.
Decision to Grant a Patent dated Mar. 2, 2021 for corresponding Japanese Application No. 2016-220377 and English translation.

* cited by examiner

SYRINGE PUMP

CROSS-REFERENCE TO RELATED APPLICATION

This application is a continuation of PCT International Application No. PCT/JP2017/037689 filed on Oct. 18, 2017 which claims the benefit of priority to Japanese Patent Application No. 2016-220377 filed on Nov. 11, 2016, the entire contents of which are herein incorporated by reference.

BACKGROUND OF THE INVENTION

1. Field of the Invention

The present invention relates to a syringe pump.

2. Description of the Related Art

A syringe pump that is used when a medical solution is injected at a low speed has been known conventionally. Such a syringe pump includes, for example, a lead screw and a slider where the slider engages with the lead screw on an engagement part thereof. Then, by rotation of the lead screw, the slider slides to move in a predetermined direction of travel to push a plunger of a syringe that contains a medical solution.

Japanese Utility Model Application Publication No. H06-55644

However, in a conventional syringe pump, when a plunger is pushed and as a slider is tilted by a load that is received from the plunger, an engagement part is also tilted to cause incomplete engagement with a lead screw, so that there is a problem in that it is not possible to push the plunger sufficiently.

SUMMARY OF THE INVENTION

A syringe pump according to an aspect of the present invention includes a lead screw and a slider. The slider has an engagement part that engages with the lead screw and a slider cover with an internal space that houses the engagement part and is formed therein and an external surface that contacts a plunger of a syringe, and slides to move in a predetermined direction of travel with rotation of the lead screw to push the plunger. Then, the slider cover has a contact part that is provided in the internal space and contacts, when the slider pushes the plunger, a location that is close to the engagement part where the location is provided on a side of the direction of travel.

DETAILED DESCRIPTION OF THE PREFERRED EMBODIMENT

Figure 1A:
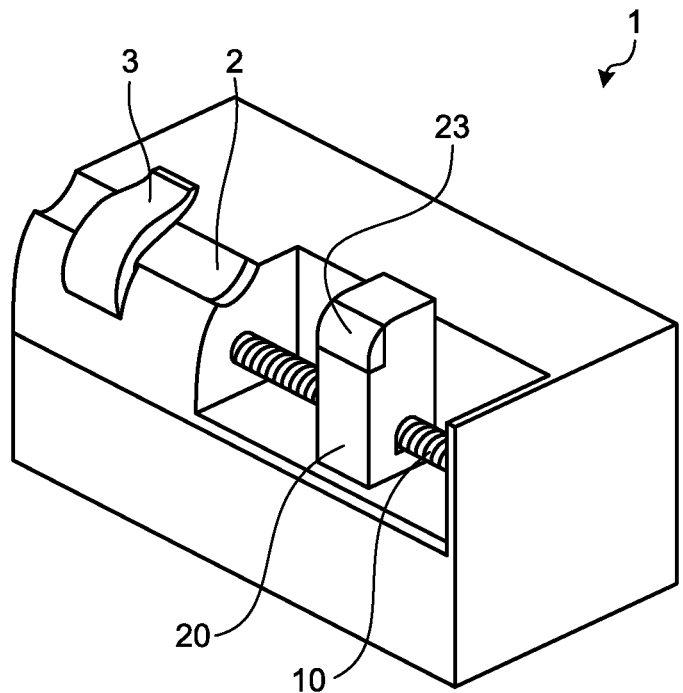
FIG. 1A is a perspective view illustrating an outline of a syringe pump according to an embodiment.

Hereinafter, a syringe pump according to an embodiment will be explained with reference to the drawings. Additionally, a relationship among dimensions of respective elements, a ratio of respective elements, or the like in the drawing may be different from actual one. Furthermore, parts with mutually different relationships of dimensions or ratios may also be included among mutual drawings.

Outline of Syringe Pump

Figure 1B:
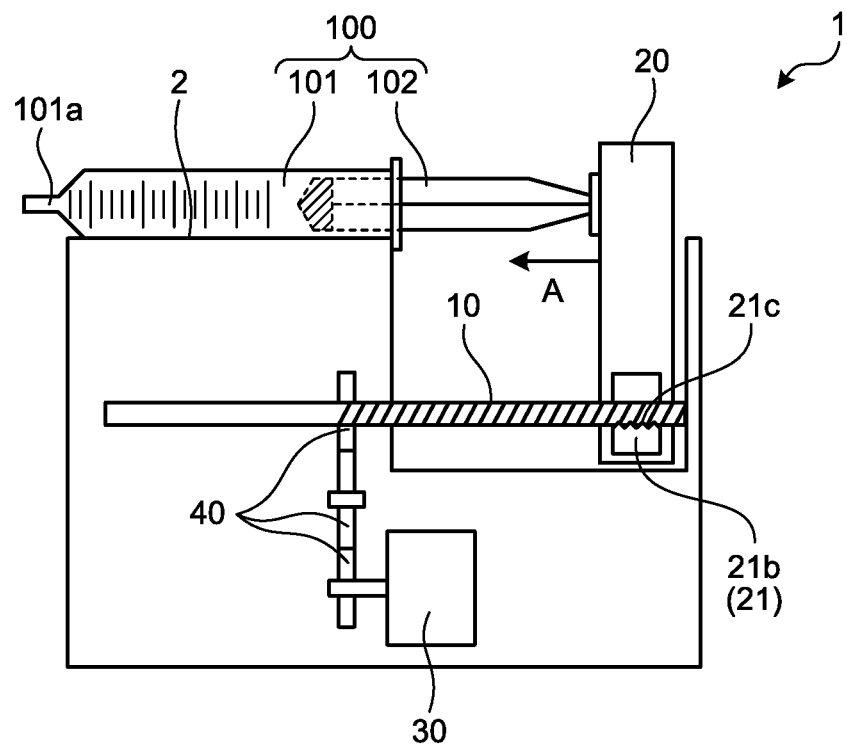
FIG. 1B is a cross-sectional view illustrating an outline of a syringe pump according to an embodiment.

First, an outline of a syringe pump 1 according to an embodiment will be explained with reference to FIG. 1A and FIG. 1B. FIG. 1A is a perspective view illustrating an outline of the syringe pump 1 according to an embodiment and FIG. 1B is a cross-sectional view illustrating an outline of the syringe pump 1 according to an embodiment.

The syringe pump 1 includes a lead screw 10 and a slider 20. A shaft of the lead screw 10 is supported so as to be rotatable at a predetermined location on the syringe pump 1. Then, for example, a driving force from a motor 30 such as a Hybrid (HB) motor or a stepping motor is transmitted through a gear group 40 so as to rotate in a predetermined direction of rotation. Furthermore, a spiral groove is formed on the lead screw 10 and an axis of rotation thereof extends in a predetermined direction.

The slider 20 has an engagement part 21c that is configured to be capable of engaging with the lead screw 10. In the present embodiment, the engagement part 21c is a site with a tooth shape that is provided on a half nut 21b of a clutch part 21 and such a site with a tooth shape has a shape to engage with a spiral groove of the lead screw 10.

Then, in a state where the engagement part 21c of the slider 20 engages with a spiral groove of the lead screw 10, as the lead screw 10 rotates in a predetermined direction of rotation, the slider 20 slides to move in a direction of travel A thereof. Herein, such a direction of travel A is parallel to an axial direction of the lead screw 10 and is a direction to approach a placing table 2.

Herein, in the syringe pump 1, a syringe 100 is set on the placing table 2 with a recess shape that is provided at a predetermined location and the syringe 100 is fixed by a clamp 3 that is provided to be adjacent to the placing table 2. Furthermore, when the syringe 100 is set, the slider 20 is arranged so as to contact an end of a plunger 102 of the syringe 100 as illustrated in FIG. 1B.

Then, the lead screw 10 is rotated in a predetermined direction of rotation by a driving force from the motor 30 and the slider 20 slides to move in the direction of travel A, so that the plunger 102 is pushed toward a side of a syringe cylinder 101 and a medical solution that is contained in the syringe cylinder 101 is injected into a predetermined location through a distal end 101a thereof.

Herein, in a case where the slider 20 is moved and arranged so as to contact an end of the plunger 102 and as the engagement part 21c engages with the lead screw 10, it is not possible to move the slider 20 manually and quickly.

Hence, in the slider 20, a switching part 23 as illustrated in FIG. 1A is operated to move the clutch part 21 where the engagement part 21c is provided thereon, so that it is possible to switch between a state where it is connected to the lead screw 10 (that will also be called a "connection state" below) and a state where it is disconnected from the lead screw 10 (that will also be called a "disconnection state" below).

Configuration of Clutch Part

Next, a specific configuration of a clutch part 21 and a switching part 23 that are configured to be capable of switching between a connection state and a disconnection state will be explained with reference to FIG. 2A and FIG. 2B. Additionally, a slider cover 22 (see FIG. 3) that covers the clutch part 21 is not illustrated in FIG. 2A and FIG. 2B to facilitate understanding thereof.

Figure 2A:
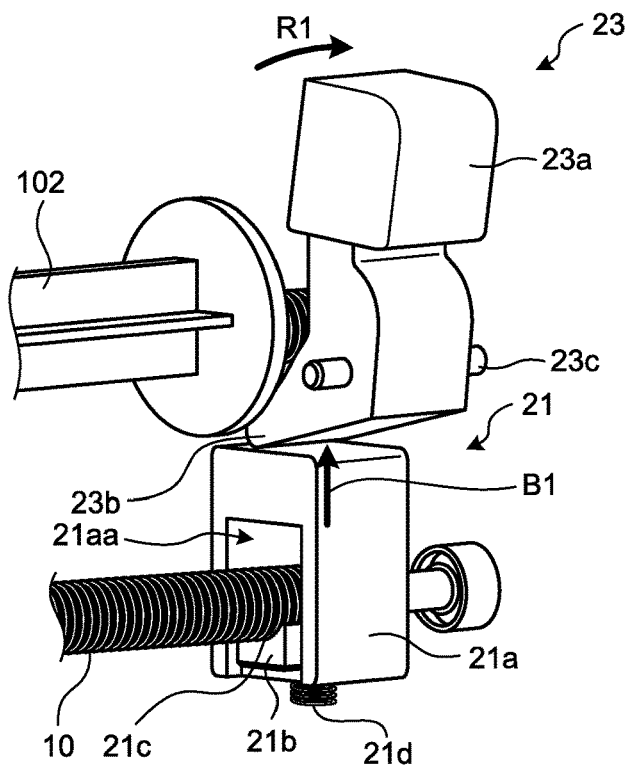
FIG. 2A is a diagram illustrating a state (a connection state) where a lead screw engages with an engagement part of a clutch part to connect the lead screw to the clutch part.

FIG. 2A is a diagram illustrating a state where a lead screw 10 engages with an engagement part 21c of the clutch part 21 to connect the lead screw 10 to the clutch part 21 (a connection state).

The clutch part 21 includes a body part 21a, a half nut 21b, and a pressing part 21d. A through-hole 21aa that penetrates through the body part 21a with a rectangular shape in an axial direction of the lead screw 10 is formed therein and the lead screw 10 is inserted through such a through-hole 21aa. Furthermore, the half nut 21b is fixed on a surface on an opposite side of the switching part 23 among inner wall surfaces around the through-hole 21aa. Then, an engagement part 21c that is of a tooth shape is provided on surface of such a half nut 21b on a side of the switching part 23.

In an embodiment, for example, the body part 21a is formed of a resin and the half nut 21b is formed of a metal. Thus, in an embodiment, the body part 21a and the half nut 21b are composed of separate members and the engagement part 21c is provided on the half nut 21b that is a member separate from the body part 21a.

However, for example, the body part 21a may be formed of a metal to provide the engagement part 21c on the body part 21a directly. Thus, at least the engagement part 21c is composed of a metal, so that, when a load from a plunger 102 is applied thereto, it is possible to realize stable engagement with the lead screw 10 without breaking a tooth of the engagement part 21c.

Moreover, the clutch part 21 is provided with the pressing part 21d that is composed of a spring or the like. For example, one end side of the pressing part 21d is supported by the body part 21a and the other end side is supported at a predetermined position on the slider cover 22. Then, such a pressing part 21d presses the clutch part 21 in a direction B1 (an upward direction in the figure) that is a direction different from an axial direction of the lead screw 10 and that is a direction toward the switching part 23.

Herein, due to pressing in the direction B1 by the pressing part 21d, the clutch part 21 is pressed toward the direction B1. Thereby, a state (that is, a connection state) is realized where the half nut 21b contacts the lead screw 10 and the engagement part 21c engages with the lead screw 10.

Furthermore, the switching part 23 is arranged on the clutch part 21 on a side of the direction B1. The switching part 23 has an operation part 23a that is provided to be distant from the clutch part 21 and a pushing part 23b that is provided near the clutch part 21. Furthermore, the switching part 23 is provided with a shaft support part 23c between the operation part 23a and the pushing part 23b. Then, the switching part 23 is supported so as to be rotatable around the shaft support part 23c as a shaft.

Herein, in a connection state, the switching part 23 is not operated by an operator or the like, and hence, is pushed by the clutch part 21 toward the direction B1. Then, in the switching part 23, the operation part 23a and the pushing part 23b are rotated in a direction of rotation R1 around the shaft support part 23c as a shaft.

Figure 2B:
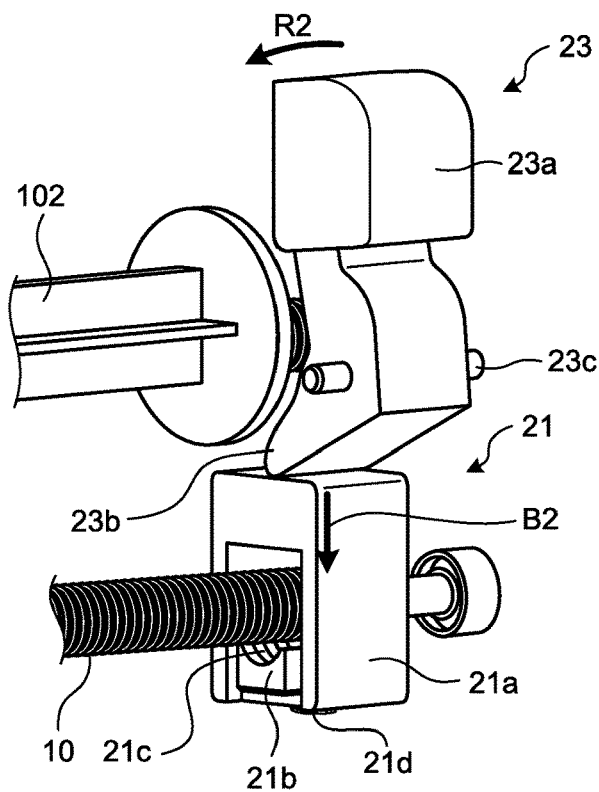
FIG. 2B is a diagram illustrating a state (a disconnection state) where a lead screw is separated from an engagement part of a clutch part to disconnect the lead screw from the clutch part.

FIG. 2B is a diagram illustrating a state where the lead screw 10 is separated from the engagement part 21c of the clutch part 21 to disconnect the lead screw 10 from the clutch part 21 (a disconnection state).

For switching from a connection state as described above to a disconnection state, for example, an operator operates the operation part 23a of the switching part 23 to rotate such an operation part 23a in a direction of rotation R2 that is an opposite direction of the direction of rotation R1. Accordingly, the pushing part 23b of the switching part 23 also rotates in the direction of rotation R2 around the shaft support part 23c as a shaft to push the clutch part 21 that is adjacent to a side of the direction of rotation R2.

Herein, as a force that is greater than a pressing force in the direction B1 by the pressing part 21d is applied from the pushing part 23b, the clutch part 21 moves in a direction B2 that is an opposite direction of the direction B1. Thereby, a state (that is, a disconnection state) is realized where the half nut 21b is separated from the lead screw 10 and the engagement part 21c does not engage with the lead screw 10.

Thus, according to an embodiment, in such a disconnection state, it is possible for an operator to move the slider 20 manually and quickly and arrange the slider 20 so as to contact an end of the plunger 102.

Additionally, in a disconnection state as described above, as arrangement of the slider 20 is completed and an operator stops an operation of the operation part 23a, the clutch part 21 is pressed in the direction B1 so that the half nut 21b contacts the lead screw 10. Thereby, a state where the engagement part 21c engages with the lead screw 10 (that is, a connection state) is provided again.

Detailed Configuration of Slider

Next, a detailed configuration of the slider 20, in particular, the slider cover 22, in the syringe pump 1 will be explained by using FIG. 3 to FIG. 5. Hereinafter, first, arrangement of each site in a state where a load is not received from the plunger 102 will be explained in FIG. 3, and then, a positional relationship among respective sites in a state where a load from the plunger 102 is applied thereto will be explained in FIG. 4. Then, a positional relationship among respective sites in a state where a greater load from the plunger 102 is applied thereto will be explained in FIG. 5.

Figure 3:
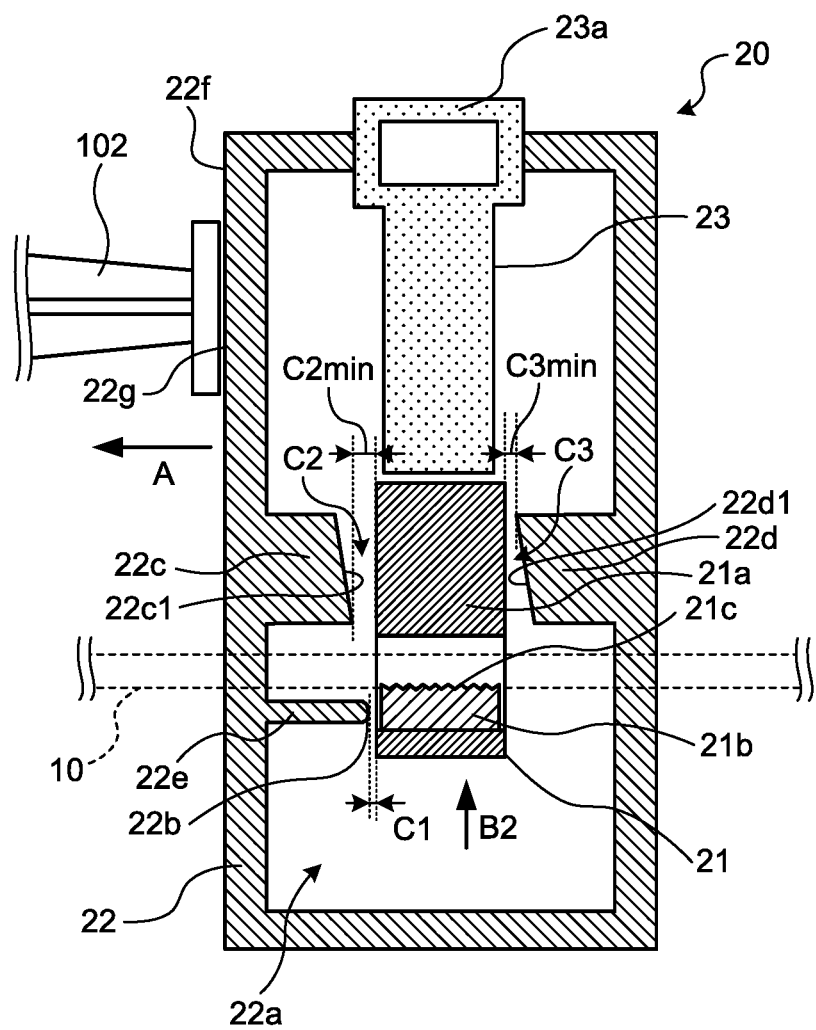
FIG. 3 is a cross-sectional view of a slider according to an embodiment.

FIG. 3 is a cross-sectional view of a slider 20 according to an embodiment. Additionally, FIG. 3 is a cross-sectional view of the slider 20 that is cut by a plane that is parallel to an axial direction of a lead screw 10 and parallel to a direction B1, B2 where a clutch part 21 moves therein. Furthermore, FIG. 3 illustrates a state where the slider 20 is not slid to move in a direction of travel A thereof and a load is not received from a plunger 102, in a connection state where the clutch part 21 moves in the direction B2.

As illustrated in FIG. 3, the slider 20 has a clutch part 21, a slider cover 22, and a switching part 23. Then, the clutch part 21 and the switching part 23 are placed at predetermined locations in an internal space 22a that is formed inside the slider cover 22. That is, the slider cover 22 covers a whole of the clutch part 21 and a part of an operation part 23a of the switching part 23 except another part thereof.

Furthermore, the clutch part 21 and the switching part 23 are supported at respective predetermined locations on the slider cover 22. For example, the clutch part 21 is supported by the slider cover 22 through a pressing part 21*d* (see FIG. 2A) and the switching part 23 is supported by the slider cover 22 through a shaft support part 23*c* (see FIG. 2A).

Herein, the slider cover 22 has a contact part 22*b* and a pair of guide ribs 22*c*, 22*d* on a side of the internal space 22*a*. For example, the contact part 22*b* is provided on a tip part of a protrusion part 22*e* that is formed on a side of the internal space 22*a* of the slider cover 22 and provided to be close to a side of the direction of travel A with respect to an engagement part 21*c* on the clutch part 21.

For example, the contact part 22*b* is provided to be close to a side of the direction of travel A with respect to a side surface of a body part 21*a* that is close to the engagement part 21*c* on a side of the direction of travel A and a clearance C1 with a predetermined dimension is formed between the contact part 22*b* and the body part 21*a*.

The pair of guide ribs 22*c*, 22*d* is provided so as to protrude toward the clutch part 21 on a side of the internal space 22*a* of the slider cover 22. In the pair of guide ribs 22*c*, 22*d*, a guide rib 22*c* is provided to be close to a side of the direction of travel A with respect to the clutch part 21. Furthermore, the other guide rib 22*d* is provided to be close to an opposite side of the direction of travel A with respect to the clutch part 21. Then, the pair of guide ribs 22*c*, 22*d* has a function to guide reciprocation of the clutch part 21 in the direction B1 and the direction B2 as illustrated in FIG. 2A and FIG. 2B.

Herein, as illustrated in FIG. 3, a first tilt part 22*c*1 is provided on a side surface of the guide rib 22*c* that faces the clutch part 21. Such a first tilt part 22*c*1 is configured to tilt in such a manner that a distance from the clutch part 21 is decreased as it approaches the engagement part 21*c*. Furthermore, the first tilt part 22*c*1 is configured to increase a distance from the clutch part 21 as it approaches a plunger contact part 22*g* of the slider cover 22 that contacts the plunger 102 on an external surface 22*f* of the slider cover 22.

Then, a clearance C2 with a predetermined dimension is formed between such a first tilt part 22*c*1 and the clutch part 21. Such a clearance C2 is formed to be a minimum value C2 min where a distance on a side of the lead screw 10 is smallest as described above. Herein, the minimum value C2 min of the clearance C2 is set so as to be greater than the clearance C1 between the contact part 22*b* and the body part 21*a*. Its reason will be described later.

Moreover, a second tilt part 22*d*1 is also provided on a side surface of the other guide rib 22*d* that faces the clutch part 21. Such a second tilt part 22*d*1 is configured to tilt in such a manner that a distance from the clutch part 21 is increased as it approaches the engagement part 21*c*. In other words, the second tilt part 22*d*1 is configured to decrease a distance from the clutch part 21 as it approaches the plunger contact part 22*g*.

Then, a clearance C3 with a predetermined dimension is formed between such a second tilt part 22*d*1 and the clutch part 21. Such a clearance C3 is formed to be a minimum value C3 min where a distance on a side of the plunger contact part 22*g* is smallest as described above. Herein, the minimum value C3 min of the clearance C3 is set so as to be less than the minimum value C2 min of the clearance C2 as described above.

Thereby, when the clutch part 21 is reciprocated, it is possible to decrease backlash of the clutch part 21 on a side of the guide rib 22*d*, so that it is possible to reciprocate the clutch part 21 stably. Therefore, it is possible to switch between a connection state and a disconnection state stably.

Next, a positional relationship among respective sites in a case where a plunger 102 is pushed by a slider 20 configured as described above and a load is received from the plunger 102 will be explained by using FIG. 4. FIG. 4 is a cross-sectional view illustrating a state at a time when a load L1 is received from the plunger 102 in the slider 20.

Figure 4:
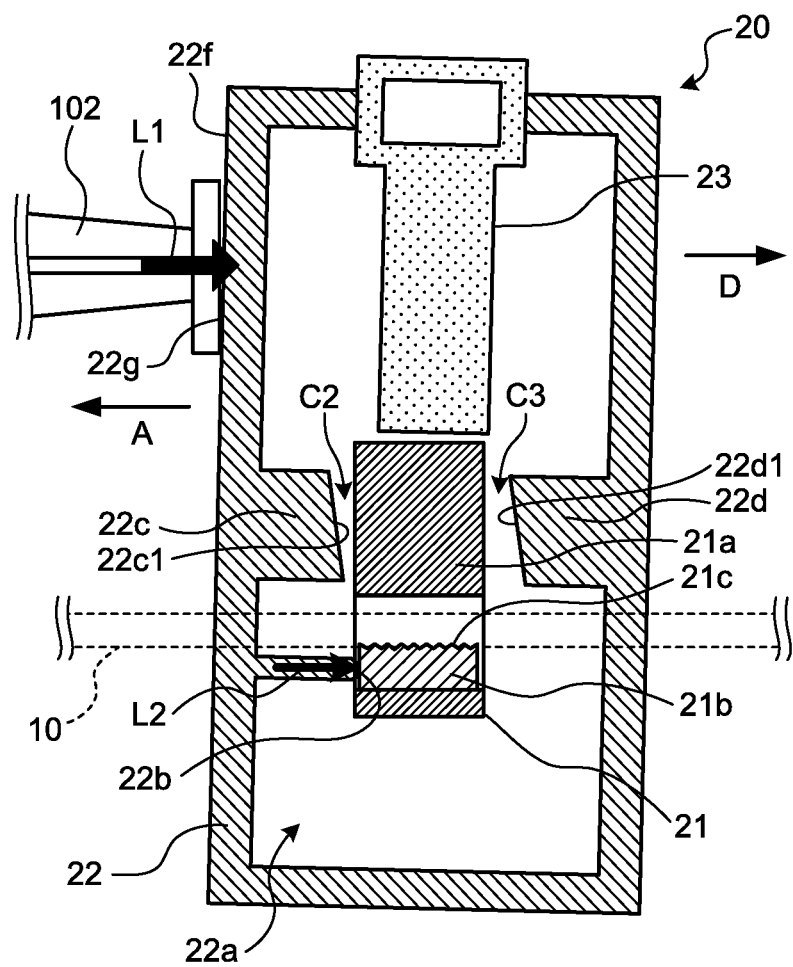
FIG. 4 is a cross-sectional view illustrating a state a time when a load is received from a plunger in a slider according to an embodiment.

As illustrated in FIG. 4, by the load L1 from the plunger 102 that is applied to a plunger contact part 22*g*, a slider cover 22 is slid to move in a direction D that is opposite to a direction of travel A and tilted toward the direction D around an engagement part 21*c* as a center. That is because the load L1 acts in the direction D that is opposite to the direction of travel A and the engagement part 21*c* that engages with a lead screw 10 acts as a point of support.

Herein, the slider cover 22 is pushed by the plunger 102 and slid to move to a side of the direction D that is opposite to the direction of travel A, so that a contact part 22*b* of the slider cover 22 contacts a side surface of a body part 21*a* on a side of the direction of travel A. That is because the contact part 22*b* is provided to be close to a side of the direction of travel A with respect to a side surface of the body part 21*a* on a side of the direction of travel A and a clearance C1 between the contact part 22*b* and the body part 21*a* is less than a minimum value C2 min of a clearance C2 between a first tilt part 22*c*1 and a clutch part 21.

In other words, the clearance C1 is set to be less than the minimum value C2 min of the clearance C2 so that it is possible to cause the contact part 22*b* to contact the body part 21*a* reliably without causing a guide rib 22*c* to contact the clutch part 21.

Then, the contact part 22*b* contacts the body part 21*a*, so that it is possible to transmit a load L2 that is caused by the load L1 from the plunger 102 to the body part 21*a* through the contact part 22*b*. Herein, the contact part 22*b* contacts the body part 21*a* that is close to the engagement part 21*c* that is a point of support, so that a point of action where the load L2 acts thereon is a position that is close to such a point of support.

Thus, a point of action of a force is close to a point of support thereof inside the slider cover 22, so that it is possible to decrease a moment of a force that acts on the slider cover 22. Thereby, it is possible to decrease a force in a direction where the slider cover 22 is tilted therein (that is, the direction D), so that it is possible to suppress tilting of the slider cover 22.

Therefore, it is also possible to suppress tilting of the clutch part 21 that is supported by the slider cover 22, so that it is possible to suppress tilting of the engagement part 21*c* of the clutch part 21 and maintain a state of good engagement between the engagement part 21*c* and the lead screw 10 and it is possible to suppress tooth breaking or tooth jumping.

Furthermore, according to an embodiment, the engagement part 21*c* is provided on the half nut 21*b*. Accordingly, the half nut 21*b* and the body part 21*a* may be molded integrally to cause the half nut 21*b* to contact the contact part 22*b*. Thereby, it is possible to transmit the load L2 from a contact location that is a point of support to the engagement part 21*c* that is a point of support through the half nut 21*b* that is made of a metal with a high rigidity.

Therefore, it is possible to stably transmit the load L2 to the engagement part 21*c* that is a point of support, so that it is possible to stably maintain a state of good engagement between the engagement part 21*c* and the lead screw 10.

Furthermore, as illustrated in FIG. 3, a contact surface of the contact part 22b that contacts the clutch part 21 is preferably a spherical surface shape or an R-shape. Thereby, independently of how the slider cover 22 is tilted, it is possible to cause the contact part 22b to contact the clutch part 21 in a manner of point contact or line contact, so that it is possible to cause a point of action (a point contact location or a line contact location) to be close to a point of support (the engagement part 21c).

Therefore, according to an embodiment, a contact surface of the contact part 22b is provided as a spherical surface shape or an R-shape, so that it is possible to suppress tilting of the clutch part 21 independently of how the slider cover 22 is tilted.

Next, a positional relationship among respective sites in a case where a load L1 from a plunger 102 is changed to a greater load L1a (for example, 10 kg) will be explained by using FIG. 5. FIG. 5 is a cross-sectional view illustrating a state where a slider 20 receives the greater load L1a from the plunger 102.

Figure 5:
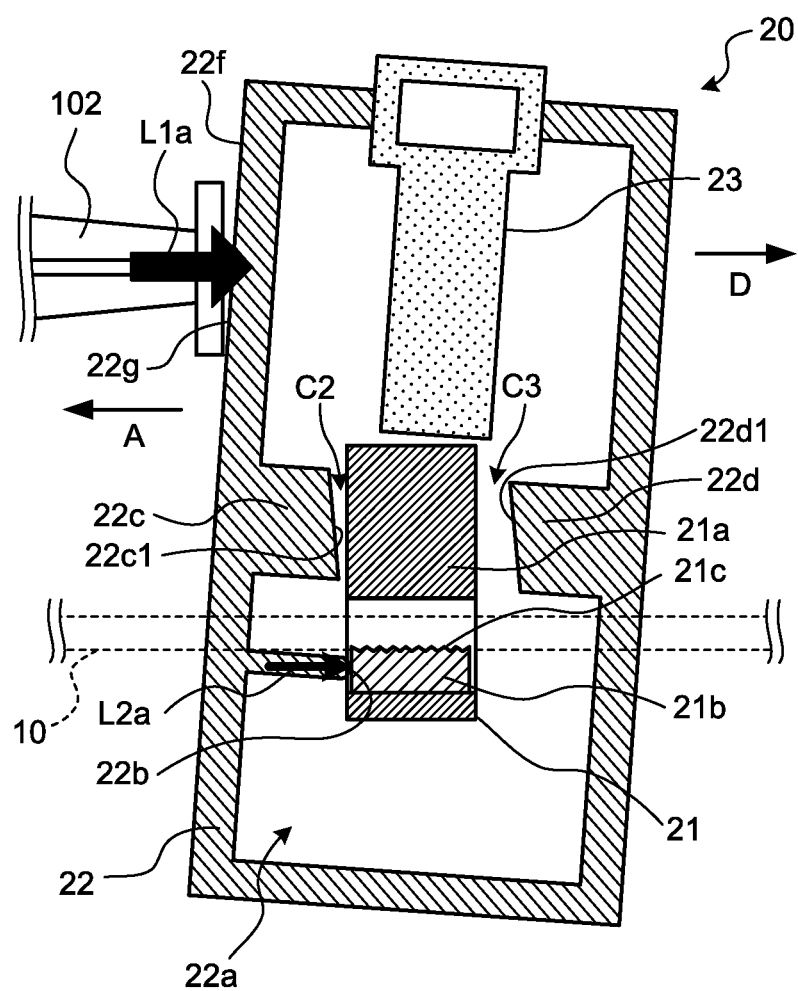
FIG. 5 is a cross-sectional view illustrating a state at a time when a greater load is received from a plunger in a slider according to an embodiment.

As illustrated in FIG. 5, a slider cover 22 is tilted in a direction D that is opposite to a direction of travel A around an engagement part 21c as a center by the load L1a from the plunger 102 that is applied to a plunger contact part 22g. Herein, the load L1a is greater than a load L1 as illustrated in FIG. 4, so that a tilt of the slider cover 22 toward the direction D is greater than a tilt of the slider cover 22 as illustrated in FIG. 4.

Herein, in an embodiment, a first tilt part 22c1 is provided on a guide rib 22c, so that it is possible to maintain a clearance C2 between the guide rib 22c and a clutch part 21 even in a case where a tilt of the slider cover 22 is increased as illustrated in FIG. 5.

If the first tilt part 22c1 is not provided on the guide rib 22c, an upper end of such a guide rib on a side of a direction of travel contacts a body part as a tilt of the slider cover 22 is increased. Then, a load from a plunger is transmitted to such a contact location. That is, such a contact location is provided as a point of action of a force.

Then, in such a case, a point of action of a force is separated from an engagement part that is a point of support thereof, so that a moment of a force that acts on a slider cover is increased. Thereby, a force in a direction to tilt a slider cover is increased, so that the slider cover is greatly tilted toward the direction D.

Therefore, a clutch part that is supported by a slider cover is also tilted greatly, and as a result, an engagement part is also tilted greatly, so that engagement between such an engagement part and a lead screw is incomplete and it may be impossible to push a plunger sufficiently.

However, in an embodiment, as described above, even in a case where the load L1a is applied to tilt the slider cover 22, the first tilt part 22c1 that is configured to ensure the clearance C2 with the clutch part 21 is provided on the guide rib 22c. Thereby, it is possible to transmit a load L2a that is caused by the load L1a to the engagement part 21c continuously through a contact part 22b that is close to the engagement part 21c.

Therefore, according to an embodiment, it is possible to maintain a point of action of a force at a location in the slider 20 that is close to the engagement part 21c, so that it is possible to suppress tilting of the clutch part 21.

Moreover, in an embodiment, a second tilt part 22d1 is provided on a guide rib 22d, so that it is possible to maintain a clearance C3 between the guide rib 22d and the clutch part 21 even in a case where a tilt of the slider cover 22 is increased as illustrated in FIG. 5.

If the second tilt part 22d1 is not provided on the guide rib 22d, a lower end of a guide rib on an opposite side of a direction of travel contacts a body part as a tilt of the slider cover 22 is increased. Then, a load from a plunger is transmitted to such a contact location.

Then, in such a case, such a contact position is separated from an engagement part, so that a moment of a force that acts on a slider cover is increased. Thereby, a slider cover is tilted greatly. Therefore, a clutch part that is supported by a slider cover is also tilted greatly, and as a result, an engagement part is also tilted greatly, so that engagement between such an engagement part and a lead screw may be incomplete.

However, in an embodiment, as described above, the second tilt part 22d1 configured to ensure the clearance C3 with the clutch part 21 even in a case where the load L1a is applied to tilt the slider cover 22 greatly is provided on the guide rib 22d. Thereby, it is possible to transmit the load L2a that is caused by the load L1a to the engagement part 21c continuously through the contact part 22b that is close to the engagement part 21c.

Therefore, according to an embodiment, it is possible to maintain a point of action of a force at a location on the slider 20 that is close to the engagement part 21c, so that it is possible to suppress tilting of the clutch part 21.

Additionally, in an embodiment, as described above, the first tilt part 22c1 is configured in such a manner that a distance from the clutch part 21 is decreased as it approaches the engagement part 21c.

This is because the plunger contact part 22g is arranged above the engagement part 21c so that the slider cover 22 is tilted toward the direction D that is opposite to the direction of travel A by a load from the plunger 102. That is, in an embodiment, the first tilt part 22c1 may be tilted toward an opposite direction (in such a case, the direction of travel A) of a direction where the slider cover 22 is tilted therein (in such a case, the direction D) and provided on the guide rib 22c.

On the other hand, in a case where the plunger contact part 22g is arranged below the engagement part 21c, the slider cover 22 is tilted toward the direction of travel A by a load from the plunger 102. In such a case, in order to prevent the guide rib 22c from contacting the clutch part 21, the first tilt part 22c1 is preferably tilted toward an opposite direction (in such a case, the direction D) of a direction where the slider cover 22 is tilted therein (in such a case, the direction of travel A) and provided on the guide rib 22c.

That is, a direction where the slider cover 22 is tilted by a load from the plunger 102 is determined by a positional relationship between the plunger contact part 22g and the engagement part 21c. Then, the first tilt part 22c1 is preferably provided to be tilted toward an opposite direction of a direction where the slider cover 22 is tilted therein. Moreover, the second tilt part 22d1 is also preferably provided to be similarly tilted toward an opposite direction of a direction where the slider cover 22 is tilted therein.

In an embodiment, although an example where tilt shapes (the first tilt part 22c1, the second tilt part 22d1) are provided on both of the guide ribs 22c, 22d as a pair has been illustrated, a tilt shape is not necessarily provided on both of the guide ribs 22c, 22d. For example, a tilt shape (the first tilt part 22c1 or the second tilt part 22d1) may be provided on only one of the guide ribs 22c, 22d as a pair.

In an embodiment, as illustrated in FIG. 5, the slider cover 22 is tilted toward the direction D that is opposite to the direction of travel A by the load L1a from the plunger 102, so that the clearance C2 as a gap on a side of the direction of travel A with respect to the clutch part 21 may be less than the clearance C3 on an opposite side thereof.

In a case where such a situation is taken into consideration, at least the first tilt part 22c1 is provided on the guide rib 22c on a side of the direction of travel A, so that it is possible to suppress contact between the clutch part 21 and the guide rib 22c.

Variation

Figure 6:
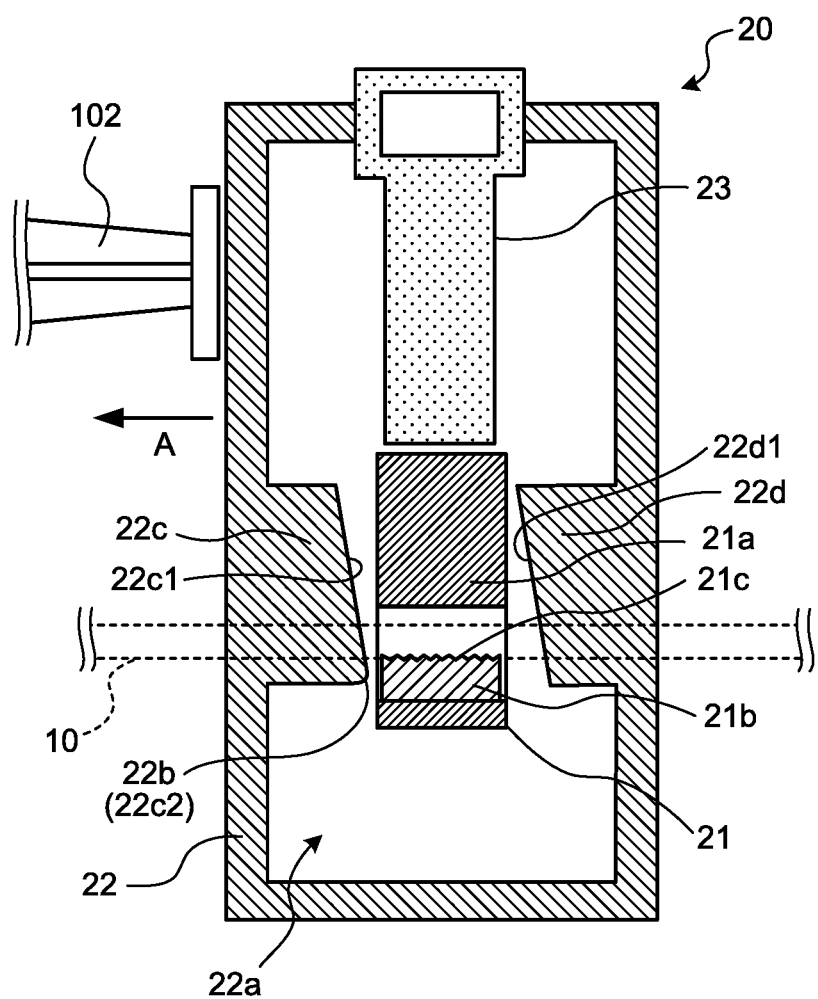
FIG. 6 is a cross-sectional view of a slider according to a variation of an embodiment.

Next, a variation of the syringe pump 1 according to an embodiment will be explained by using FIG. 6. FIG. 6 is a cross-sectional view of a slider 20 according to a variation of an embodiment and a diagram that corresponds to FIG. 3 for an embodiment.

In the slider 20 according to a variation, shapes of a contact part 22b and a pair of guide ribs 22c, 22d of a slider cover 22 are different from those of an embodiment as described above. Sites other than the contact part 22b and the guide ribs 22c, 22d are similar to those of such an embodiment, so that a detailed explanation of such other sites will be omitted.

In the slider 20 according to a variation, the guide ribs 22c, 22d are arranged so as to extend to a height where it is adjacent to an engagement part 21c of a clutch part 21. Additionally, in a variation, the guide ribs 22c, 22d are provided at a position where they do not interfere with a lead screw 10. Then, an end part 22c2 of a first tilt part 22c1 on a side that is close to the engagement part 21c is close to a side of a direction of travel A with respect to a side surface of a body part 21a that is close to the engagement part 21c on a side of the direction of travel A.

Due to such a configuration of the first tilt part 22c1, it is possible to cause the end part 22c2 of the first tilt part 22c1 to function as the contact part 22b in an embodiment. In other words, in a variation, the contact part 22b is provided integrally with a guide rib 22c on a side of the direction of travel A.

Herein, according to a variation, it is possible to form the guide rib 22c and the contact part 22b integrally, so that it is possible to simplify a shape of a mold for injection-molding the slider cover 22.

Furthermore, as illustrated in FIG. 6, the end part 22c2 that functions as the contact part 22b may be of a spherical surface shape or an R-shape. Thereby, independently of how the slider cover 22 is tilted, it is possible to cause the contact part 22b (the end part 22c2) to contact the clutch part 21 in a manner of point contact or line contact, so that it is possible to cause a point of action (a point contact location or a line contact location) to be close to a point of support (the engagement part 21c).

Therefore, according to a variation, the end part 22c2 is provided as a spherical surface shape or an R-shape, so that it is possible to suppress tilting of the clutch part 21 independently of how the slider cover 22 is tilted.

Additionally, in a variation as described above, both of guide ribs 22c, 22d as a pair are arranged so as to extend to a height where they are adjacent to the engagement part 21c. However, a guide rib 22d on an opposite side of the direction of travel A is not necessarily arranged at a height where it is adjacent to the engagement part 21c.

As described above, according to an embodiment, the contact part 22b is provided on the slider cover 22 and the contact part 22b is caused to contact a location that is close to the engagement part 21c when the plunger 102 is pushed, so that it is possible to cause a point of support of a force to be close to a point of action thereof inside the slider cover 22. Thereby, it is possible to decrease a moment of a force that acts on the slider cover 22, so that it is possible to suppress tilting of the slider cover 22. Therefore, when the plunger 102 is pushed, it is possible to suppress tilting of the engagement part 21c and maintain a state of good engagement between the engagement part 21c and the lead screw 10.

Additionally, although an embodiment as described above is configured in such a manner that the switching part 23 is rotated while the shaft support part 23c is an axis thereof and thereby the clutch part 21 is pushed to separate from the lead screw 10, a configuration of the switching part 23 is not limited thereto.

For example, a configuration may be provided in such a manner that the switching part 23 is configured in such a manner that it is possible to slide to move in a direction that is identical to the direction B1, B2 of reciprocation of the clutch part 21 and the switching part 23 is pushed toward a side of the clutch part 21 so that the clutch part 21 is separated from the lead screw 10.

As described above, a syringe pump 1 according to an embodiment has a lead screw 10 and a slider 20. The slider 20 has an engagement part 21c that engages with the lead screw 10 and a slider cover 22 with an internal space 22a that houses the engagement part 21c and is formed therein and an external surface 22f that contacts a plunger 102 of a syringe 100, and slides to move in a predetermined direction of travel A with rotation of the lead screw 10 to push the plunger 102. Then, the slider cover 22 has a contact part 22b that is provided in the internal space 22a and contacts, when the slider 20 pushes the plunger 102, a location that is close to the engagement part 21c where the location is provided on a side of the direction of travel A. Thereby, it is possible to suppress tilting of the engagement part 21c when the plunger 102 is pushed and to maintain a state of good engagement between the engagement part 21c and the lead screw 10, so that it is possible to suppress tooth breaking or tooth jumping.

Furthermore, in the syringe pump 1 according to an embodiment, the slider 20 further has a clutch part 21 that reciprocates in a direction B1, B2 that is different from an axial direction of the lead screw 10 to switch between a state where it is connected to the lead screw 10 and a state where it is disconnected from the lead screw 10. Then, the engagement part 21c is provided on the clutch part 21. Thereby, it is possible for an operator to move the slider 20 manually and quickly and arrange the slider 20 so as to contact an end of the plunger 102.

Furthermore, in the syringe pump 1 according to an embodiment, the slider cover 22 has a pair of guide ribs 22c, 22d that are provided to be close to the clutch part 21 on a side of the direction of travel A and an opposite side of the direction of travel A, respectively, and guide reciprocation of the clutch part 21. Then, a guide rib 22c that is provided on a side of the direction of travel A with respect to the clutch part 21 has a first tilt part 22c1 that tilts so as to ensure a clearance C2 with the clutch part 21 in a case where the slider 20 pushes the plunger 102 to tilt the slider cover 22. Thereby, it is possible to suppress tilting of the clutch part 21.

Furthermore, in the syringe pump 1 according to an embodiment, a minimum value C2 min of the clearance C2 between the clutch part 21 and the first tilt part 22c1 is greater than a clearance C1 between the clutch part 21 and the contact part 22b in a state where the slider 20 does not push the plunger 102. Thereby, it is possible to cause the contact part 22b to contact a half nut 21b reliably without causing the guide rib 22c to contact the clutch part 21.

Furthermore, in the syringe pump 1 according to an embodiment, a guide rib 22d that is provided on an opposite side of the direction of travel A with respect to the clutch part 21 has a second tilt part 22d1 that tilts to ensure a clearance C3 with the clutch part 21 in a case where the slider 20 pushes the plunger 102 to tilt the slider cover 22. Thereby, it is possible to suppress tilting of the clutch part 21.

Furthermore, in the syringe pump 1 according to an embodiment, the minimum value C2 min of the clearance C2 between the clutch part 21 and the first tilt part 22c1 is greater than a minimum value C3 min of the clearance C3 between the clutch part 21 and the second tilt part 22d1 in a state where the slider 20 does not push the plunger 102. Thereby, it is possible to reciprocate the clutch part 21 stably, so that it is possible to switch between a connection state and a disconnection state stably.

Furthermore, in a syringe pump 1 according to a variation of an embodiment, a contact part 22b is provided integrally with a guide rib 22c that is provided on a side of a direction of travel A with respect to a clutch part 21. Thereby, it is possible to simplify a shape of a slider 20.

Furthermore, in the syringe pump 1 according to a variation of an embodiment, the clutch part 21 is provided in such a manner that a half nut 21b where an engagement part 21c is provided thereon and an body part 21a thereof are molded integrally, and a contact part 22b contacts the half nut 21b when a plunger 102 is pushed. Thereby, it is possible to maintain a state of good engagement between the engagement part 21c and a lead screw 10 stably.

According to an aspect of the present invention, it is possible to suppress tilting of an engagement part when a plunger is pushed.

Furthermore, the present invention is not limited by an embodiment as described above. A configuration provided by appropriately combining respective components is also included in the present invention. Furthermore, it is possible for a person skilled in the art to readily derive an additional effect or variation. Hence, a broader aspect of the present invention is not limited to an embodiment as described above and a variety of modifications thereto are allowed.

What is claimed is:

1. A syringe pump, comprising:
a lead screw; and
a slider that has an engagement part that engages with the lead screw and a slider cover with an internal space that houses the engagement part and is formed therein and an external surface that contacts a plunger of a syringe, and slides to move in a predetermined direction of travel with rotation of the lead screw to push the plunger, wherein
the slider cover has a contact part that is provided in the internal space and contacts, when the slider pushes the plunger, a location that is close to the engagement part where the location is provided on a side of the direction of travel,
the slider further has a clutch part that reciprocates in a direction that is different from an axial direction of the lead screw to switch between a state where the clutch part is connected to the lead screw and a state where the clutch part is disconnected from the lead screw,
the engagement part is provided on the clutch part,
the slider cover has a pair of guide ribs that are provided to be close to the clutch part on the side of the direction of travel and an opposite side of the direction of travel, respectively, and guide reciprocation of the clutch part, and the guide rib that is provided on the side of the direction of travel with respect to the clutch part has a first tilt part that tilts to ensure a clearance with the clutch part in a case where the slider pushes the plunger to tilt the slider cover, and
a minimum value of a clearance between the clutch part and the first tilt part is greater than a clearance between the clutch part and the contact part in a state where the slider does not push the plunger.

2. The syringe pump according to claim 1, wherein the guide rib that is provided on the opposite side of the direction of travel with respect to the clutch part has a second tilt part that tilts to ensure a clearance with the clutch part in a case where the slider pushes the plunger to tilt the slider cover.

3. The syringe pump according to claim 2, wherein the minimum value of the clearance between the clutch part and the first tilt part is greater than a minimum value of a clearance between the clutch part and the second tilt part in a state where the slider does not push the plunger.

4. The syringe pump according to claim 1, wherein the contact part is provided integrally with the guide rib that is provided on the side of the direction of travel with respect to the clutch part.

5. The syringe pump according to claim 1, wherein the clutch part is provided in such a manner that a half nut where the engagement part is provided thereon and a body part thereof are molded integrally, and the contact part contacts the half nut when the slider pushes the plunger.

* * * * *